United States Patent
Baba et al.

(10) Patent No.: US 9,304,113 B2
(45) Date of Patent: Apr. 5, 2016

(54) HEAT-RESISTANT ULTRASONIC SENSOR AND INSTALLATION METHOD THEREOF

(75) Inventors: Atsushi Baba, Tokai (JP); Yoshinori Musha, Hitachiota (JP); Masahiro Koike, Hitachi (JP)

(73) Assignee: Hitachi-GE Nuclear Energy, Ltd., Hitachi-shi (JP)

( * ) Notice: Subject to any disclaimer, the term of this patent is extended or adjusted under 35 U.S.C. 154(b) by 546 days.

(21) Appl. No.: 13/474,065

(22) Filed: May 17, 2012

(65) Prior Publication Data

US 2012/0291554 A1 Nov. 22, 2012

(30) Foreign Application Priority Data

May 19, 2011 (JP) ................................. 2011-111967

(51) Int. Cl.
| | | |
|---|---|---|
| G01H 11/08 | (2006.01) | |
| H01L 41/22 | (2013.01) | |
| G01N 29/22 | (2006.01) | |
| G01N 29/24 | (2006.01) | |

(52) U.S. Cl.
CPC ............ *G01N 29/228* (2013.01); *G01N 29/245* (2013.01); *G01N 2291/0289* (2013.01); *Y10T 29/42* (2015.01)

(58) Field of Classification Search
CPC .............. G01N 29/228; G01N 29/245; G01N 2291/0289; Y10T 29/42
USPC ..................... 73/632; 310/322, 324
See application file for complete search history.

(56) References Cited

U.S. PATENT DOCUMENTS

| | | | | |
|---|---|---|---|---|
| 4,039,743 A | * | 8/1977 | Gommans | 174/114 R |
| 4,373,119 A | * | 2/1983 | Feder | 381/190 |
| 4,701,659 A | * | 10/1987 | Fujii et al. | 310/334 |
| 4,948,552 A | * | 8/1990 | Mollot et al. | 376/246 |
| 6,303,868 B1 | * | 10/2001 | Kawai | 174/128.1 |
| 6,674,011 B2 | * | 1/2004 | Ueno et al. | 174/128.1 |

FOREIGN PATENT DOCUMENTS

| | | |
|---|---|---|
| JP | 61-223518 A | 10/1986 |
| JP | 3-2368 A | 1/1991 |
| JP | 4-102007 U | 9/1992 |
| JP | 2986581 B2 | 1/1993 |

(Continued)

OTHER PUBLICATIONS

European Search Report dated Aug. 20, 2012 (eight (8) pages).

(Continued)

*Primary Examiner* — J M Saint Surin
(74) *Attorney, Agent, or Firm* — Crowell & Moring LLP

(57) ABSTRACT

A heat-resistant ultrasonic sensor forms a piezo-electric ceramics film with a thickness of 0.5 mm or smaller and a Curie point of 200° C. or higher on a flexible metal plate. A thin metal film that is an electrode is attached to a top surface of the piezo-electric ceramics film and a metal wire mesh covers the thin metal film and is attached to a top surface of the thin metal film. A core of a heat-resistant coaxial cable is connected to the metal wire mesh at a connection point. The heat-resistant coaxial cable is fixed to the thin metal plate with a metal fixing member that is a ground portion. An electric insulating cover is attached to the thin metal plate and covers the piezo-electric ceramics film, the thin metal film, the metal wire mesh, the connection point, the fixing member, and the core of the coaxial cable.

12 Claims, 5 Drawing Sheets

(56) References Cited

FOREIGN PATENT DOCUMENTS

| JP | 8-223696 A | 8/1996 |
|---|---|---|
| JP | 11-304777 A | 11/1999 |
| JP | 2000-287298 | 10/2000 |
| JP | 4244172 B2 | 3/2005 |
| JP | 2005-167820 A | 6/2005 |
| JP | 2005-308691 A | 11/2005 |
| JP | 2006-258610 A | 9/2006 |
| JP | 2008-47971 A | 2/2008 |
| JP | 2010-014496 | 1/2010 |

OTHER PUBLICATIONS

M. Kobayashi et al."High-Temperature Integrated and Flexible Ultrasonic Transducers for Nondestructive Testing", NDT&E International, vol. 42, No. 2, 2009, pp. 157-161, XP-25916342.

KJ Kirk et al., "Ultrasonic Thin Film Transducers for High-Temperature NDT", Insight, vol, 47, No. 2, Feb. 2005, pp. 85-87, XP-001231237.

A. McNab et al., "Ultrasonic Transducers for High Temperature Applications", Transducer Technology for Ulstrasonic NDT Applications, IEE Proc.-Sci, vol. 145, No. 5, Sep. 1998, pp. 229-236, XP-6011525.

KJ Kirk et al., "Monolithic Arrays for Monitoring Industrial Plant at High Temperatures", Ultrasonics Research Group, Department of Electronic and Electrical Engineering, vol. 2, 1994, pp. 1125-1128, XP-32084542.

R. C. Turner et al., "Materials for High Temperature Acoustic and Vibration Sensors: A Review", Applied Acoustics, vol. 41, No. 4, 1994, pp. 299-324, XP-002579340.

Y. Ono et al., "A Piezoelectric Membrane Sensor for Biomedical Monitoring" IEEE Ultrasonics Symposium, 2006, pp. 800-803.

Tatsuya Omori et al., "Preparation of Piezoelectric PZT Micro-Discs by Sol-Gel Method", T.IEE, Japan, 2001, pp. 496-500, vol. 121-E, No. 9.

Xianfeng Du et al., "Low-Temperature Synthesis of Bismuth Titanate by an Aqueous Sol-Gel Method", Journal of the American Ceramic Society, 2008, pp. 2079-2082, vol. 91, No. 7.

Japanese Office Action with partial English translation dated Aug. 6, 2013 (Seven (7) pages).

Advanced Methods for Nondestructive Testing and Material Characterization on Jun. 19, 2006 at UMass Dartmouth, N. Dartmouth, MA published in Integrated and Flexible High Temperature Ultrasonic Transducers by Makiko Kobayashi and Cheng-Kuei Jen at the Industrial Materials Institute, National Research Council of Canada, Boucherville, Quebec, Canada J4B 6Y4.

High Temperature Ultrasonic Transducers: Review by R. Kazys, A. Voleisis and B.Voleisiene, ISSN 1392-2114 ULTRAGARSAS (Ultrasound), vol. 63, Nov. 2, 2008 and http://www.ktu.lt/ultra/journal/pdf_63_2/63-2008-No.2_01-Kazys.pdf.

High Temperature Integrated and Flexible Ultrasonic Transducers for NDT by M. Kobayashi, C.-K. Jen, J.F. Bussiere and K.-T. Wu at the 17th World Conference on Nondestructive Testing, Oct. 25-28, 2008 in Shanghai, China, and http://www.ndt.net/article/wcndt2008/papers/22 4.pdf.

* cited by examiner

HEAT-RESISTANT ULTRASONIC SENSOR AND INSTALLATION METHOD THEREOF

CLAIM OF PRIORITY

The present application claims priority from Japanese Patent application serial no. 2011-111967, filed on May 19, 2011, the content of which is hereby incorporated by reference into this application.

BACKGROUND OF THE INVENTION

1. Technical Field

The present invention relates to a heat-resistant ultrasonic sensor and an installation method thereof and more particularly to a heat-resistant ultrasonic sensor and an installation method thereof that are suitable to monitor a wall thinning, crack propagation and change in a structural materials aiming at the structural member being high temperature in operation such as a nuclear power generation plant, a thermal power generation plant, and a chemical plant is in operation

2. Background Art

Conventionally, in a plant such as a power generation plant, in the periodic inspection of the plant, lowering an inspection object part of the structural member to an inspectable temperature or predicting a reduction in temperature, the inspection object part is inspected in order to evaluate the soundness of the structural member being high temperature in operation. In the inspection, if it is a surface inspection for evaluating the soundness of the surface of the structural member, a visual inspection or eddy current inspection is used and if it is a volume inspection for evaluating the soundness of the inside or back of the structural member such as wall thinning and cracking, an ultrasonic inspection is used. However, in recent years, there is an increasing demand for continuously monitoring the soundness of the structural member in a high-temperature environment when the plant is in operation, from the viewpoint of aging of the power generation plant, improvement of the inspection efficiency, and furthermore improvement of an operation rate of the plant.

In the conventional ultrasonic inspection in the periodic inspection, when an inspection object is a pipe and the wall thinning thereof is to be inspected, or when the inspection object is a structural member having a simple shape, an ultrasonic sensor (having one piezo-electric element) of a single element is used. Further, in recent years, when a structural member having a complicated shape as an inspection object and the neighborhood of a welded portion of the structural member are inspected, an array type ultrasonic sensor (having a plurality of piezo-electric elements) is used.

In each ultrasonic sensor aforementioned, in the production process, a piezo-electric element composed of a single-crystal piezo-electric material or a composite element with a thin cylindrical piezo-electric element set with epoxy resin is adhered and fixed with an epoxy adhesive to a surface of a resin plate called a front plate. Further, a packing material is used inside the ultrasonic sensor to damp the piezo-electric element and control the wave number. The packing material often uses epoxy resin as the main component. Therefore, the ultrasonic sensor of the single element and the array type ultrasonic sensor are not generally flexible. To respond to it, in cases where an inspection object has a curved surface, when performing an inspection by placing these ultrasonic sensors against that curved surface of the inspection object, a curved surface is formed on a shoe attached to the leading edge of the front plate.

On the other hand, to perform the ultrasonic inspection for the inspection object having a curved surface, a sheet-shaped ultrasonic sensor where the front plate is composed of a flexible material (polyimide, etc.) and furthermore as a piezo-electric element to be attached to the front plate, a flexible composite material is used is proposed (for example, see 'Bendable thin perpendicular transducer, Sheet transducer' (Technical data by Imaging Supersonic Laboratories Co., Ltd.).

Furthermore, as described in Proc. of 2006 IEEE Ultrasonic Symposium "A Piezoelectric Membrane Sensor for Biochemical Monitoring" pp. 800-803, it is known that a flexible piezo-electric element can be manufactured by forming thin piezo-electric ceramics on a polyimide film using a sol-gel method.

Further, a single type ultrasonic sensor and an array type ultrasonic sensor that can be used in a high-temperature environment of a power generation plant in operation are proposed (see Japanese Patent No. 2986581, Japanese Patent No. 4244172, and Japanese Patent Application Laid-open No. 8(1996)-223696).

The heat-resistant ultrasonic sensor described in Japanese Patent No. 2986581 has a front plate made of SiC or $Si_3Na$ ceramics and a $PbNb_2O_6$ or $PbTiO_3$ piezo-electric vibrator is joined to the front plate by soldering. The heat-resistant ultrasonic sensor can be used at a high temperature of about 250° C.

The heat-resistant ultrasonic sensor described in Japanese Patent No. 4244172 has an ultrasonic vibrator composed of a piezo-electric ceramics material including barium titanate, lithium niobate, lithium tantanate, and zinc oxide, arranged between a positive electrode and a negative electrode. The heat-resistant ultrasonic sensor can be used up to 700° C. without trouble.

The heat-resistant ultrasonic sensor described in Japanese Patent Application Laid-open No. 8(1996)-223696 has a plurality of piezo-electric bodies using lead titanate ceramics as a piezo-electric material and can be used up to 300° C.

Further, an example of the installation method for attaching the heat-resistant ultrasonic sensor on a surface of an inspection object is described in Japanese Patent Application Laid-open No. 11(1999)-304777. By this installation method, a soft cushioning metal plate is disposed between the heat-resistant ultrasonic sensor and a high-temperature inspection object, and the heat-resistant ultrasonic sensor is pressed toward the surface of the inspection object, thus the soft cushioning metal plate is plastic-deformed, and the heat-resistant ultrasonic sensor is closely adhered to the inspection object.

A manufacturing method of a sol-gel film is described in T. IEE Japan, Vol. 121-E, No. 9, (2001) 'Preparation of piezo-electric PZT micro-discs by sol-gel method' and J. Am. Ceram. Soc., 91 [7] pp. 20792082 (2008) 'Low-Temperature Synthesis of Bismuth Titanate by an Aqueous SolGel Method'.

CITATION LIST

Patent Literature

[Patent Literature 1] Japanese Patent No. 2986581
[Patent Literature 2] Japanese Patent No. 4244172
[Patent Literature 3] Japanese Patent Application Laid-open No. 8(1996)-223696
[Patent Literature 4] Japanese Patent Application Laid-open No. 11(1999)-304777

Non Patent Literature

[Non Patent Literature 1] 'Bendable thin perpendicular transducer, Sheet transducer' (Technical data by Imaging Supersonic Laboratories Co., Ltd.) (http://www1.kcn.ne.jp/~isl/pdf/sheet01j.pdf)
[Non Patent Literature 2] Proc. of 2006 IEEE Ultrasonics Symposium "A Piezoelectric Membrane Sensor for Biomedical Monitoring" pp. 800-803
[Non Patent Literature 3] T. IEE Japan, Vol. 121-E, No. 9, (2001) 'Preparation of piezoelectric PZT micro-discs by sol-gel method'
[Non Patent Literature 4] J. Am. Ceram. Soc., 91 [7] pp. 20792082 (2008) 'Low-Temperature Synthesis of Bismuth Titanate by an Aqueous SolGel Method'

SUMMARY OF THE INVENTION

Technical Problem

In a plant such as a power generation plant in operation, a high-temperature structural member that is an inspection object has many members having a curved surface on an outer surface such as a pipe. Particularly, a surface of a welded portion to be inspected using the ultrasonic sensor is in a curved shape. As described in Japanese Patent Application Laid-open No. 11(1999)-304777, when disposing the soft cushioning metal plate between the heat-resistant ultrasonic sensor and a high-temperature structural member, plastic-deforming the soft cushioning metal plate, and closely adhering the heat-resistant ultrasonic sensor on the surface of the inspection object, it is necessary to dispose the soft cushioning metal plate between the heat-resistant ultrasonic sensor and the high-temperature structural member and plastic-deform it, so that the attachment of the heat-resistant ultrasonic sensor is troublesome and the attachment of the heat-resistant ultrasonic sensor onto the surface of the structural member takes a long time.

The respective ultrasonic sensors described in 'Bendable thin perpendicular transducer, Sheet transducer' (Technical data by Imaging Supersonic Laboratories Co., Ltd.) and Proc. of 2006 IEEE Ultrasonic Symposium "A Piezoelectric Membrane Sensor for Biochemical Monitoring" pp. 800-803 use an epoxy adhesive and resin and furthermore, the front plate uses polyimide, so that the upper limit heat-resistant temperature is about 80° C. Since the epoxy adhesive and resin come off from the adhered surface due to thermal damage at a temperature higher than 80° C., the ultrasonic sensors cannot transmit and receive an ultrasonic wave. Therefore, these ultrasonic sensors cannot be used for inspection of the high-temperature structural member of a plant such as a power generation plant, when in operation.

An object of the present invention is to provide a heat-resistant ultrasonic sensor and an installation method thereof capable of accurately detecting defect of a structural member of a plant in operation.

Solution to Problem

A feature of the present invention for accomplishing the above object is a structure having a flexible metal plate, a piezo-electric ceramics portion attached on the metal plate and having a thickness of 0.5 mm or smaller and a Curie point of 200° C. or higher, and an electrode member disposed on the piezo-electric ceramics portion and connected to the piezo-electric ceramics portion.

The piezo-electric ceramics portion having a thickness of 0.5 mm or smaller and a Curie point of 200° C. or higher is attached on the flexible metal plate, so that even if the metal plate is bent, the piezo-electric ceramics portion is not cracked. Therefore, when attaching the heat-resistant ultrasonic sensor on the surface having a curved surface of structural member of the plant that is an inspection object, even if the flexible metal plate of the heat-resistant ultrasonic sensor is bent in accordance with the curvature of the curved surface of the structural member, the piezo-electric ceramics portion does not come off from the metal plate and the metal plate to which the piezo-electric ceramics portion bent at the curvature is normally attached can be attached on the curved surface of the structural member along the curved surface. Therefore, the ultrasonic wave generated in the piezo-electric ceramics portion can enter efficiently the inspection object and due to the incidence of the ultrasonic wave, the reflected wave generated by the inspection object can be received efficiently by the piezo-electric ceramics portion. In addition, since the metal plate and the piezo-electric ceramics portion having a Curie point of 200° C. or higher exist, the heat-resistant ultrasonic sensor can be attached to the structural member being high temperature when the plant is in operation. Therefore, defect (cracking, wall thinning, etc.) causing to the structural member at a place where a curved face is formed on the surface of the structural member being high temperature when the plant is in operation can be detected accurately.

Preferably, it is desirable that a metal wire mesh is attached to the electrode member.

Advantageous Effect of the Invention

According to the present invention, defect causing to a structural member of a plant, being high temperature when the plant is in operation can be detected accurately.

DETAILED DESCRIPTION OF THE PREFERRED EMBODIMENTS

The embodiments of the present invention will be explained below.

Embodiment 1

Figure 1:
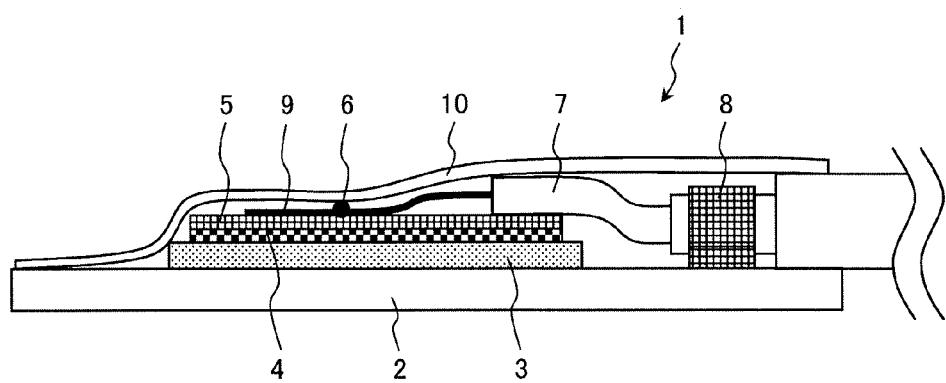
FIG. 1 is a longitudinal sectional view showing a heat-resistant ultrasonic sensor according to embodiment 1, which is a preferred embodiment of the present invention.
Figure 2:
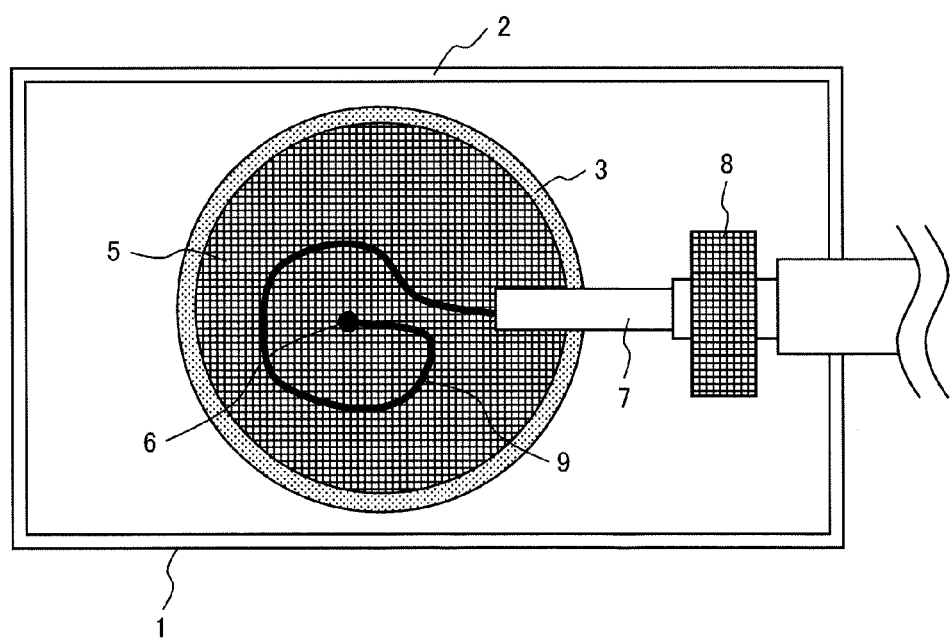
FIG. 2 is a plan view of a heat-resistant ultrasonic sensor shown in FIG. 1 in a state that an electric insulating cover is removed.

A heat-resistant ultrasonic sensor according to embodiment 1, which is a preferred embodiment of the present invention, will be explained by referring to FIGS. 1 and 2.

The heat-resistant ultrasonic sensor 1 of the present embodiment is provided with a thin metal plate (a flexible metal plate) 2, a piezo-electric ceramics film 3, a thin metal film (an electric member) 4, a metal wire mesh 5, and a coaxial cable 7. A shape of the thin metal plate 2 is rectangular and respective shapes of the piezo-electric ceramics film 3, the thin metal film 4, and the metal wire mesh 5 are circular.

The thin metal plate 2 is a flexible metal plate and for example, it is made of stainless steel with a thickness of 0.1 mm. The thin metal plate 2 is composed of a metal material having a thermal expansion coefficient of less than ±20% of the thermal expansion coefficient of the metal material composing an inspection object (for example, a pipe 12 shown in FIG. 3) to which the heat-resistant ultrasonic sensor 1 is attached. When the inspection object is made of stainless steel, it is desirable to use stainless steel for the thin metal plate 2. The reason that the metal material having a thermal expansion coefficient of less than ±20% of the thermal expansion coefficient of the metal material composing the inspection object is used for the metal material of the thin metal plate 2 is to avoid the separation of the thin metal plate 2 from the inspection object that is caused by stress generated due to the thermal expansion difference when the thermal expansion difference between the inspection object at high temperature and the thin metal plate 2 of the heat-resistant ultrasonic sensor 1 attached to the surface of the inspection object increases.

The piezo-electric ceramics film 3 is formed on one surface of the thin metal plate 2. The thin metal film 4 that is an electrode is attached to a top surface of the piezo-electric ceramics film 3. Furthermore, the metal wire mesh 5 is attached to a top surface of the thin metal film 4 and covers the thin metal film 4. A core 9 of the coaxial cable 7 is connected to the metal wire mesh 5 at a connection point 6. The coaxial cable 7 is fixed to the thin metal plate 2 with a metal fixing member 8 that is a ground portion. The electric insulating cover 10 is attached to the thin metal plate 2 and covers the piezo-electric ceramics film 3, the thin metal film 4, the metal wire mesh 5, the connection point 6, the fixing member 8, and the bare core 9 from the coaxial cable 7.

The thin metal plate 2 functions as an acoustic matching layer, so that the thickness of the thin metal plate 2 is set to the thickness smaller than or equal to the thickness obtained based on the frequency of the vibration generated by the piezo-electric ceramics of the piezo-electric ceramics film 3 formed thereon. Concretely, assuming the thickness of the thin metal plate 2 as T, the sound speed in the thin metal plate 2 as V, and the frequency of the vibration generated by the piezo-electric ceramics of the piezo-electric ceramics film 3 as F, the thickness of the thin metal plate 2 is set so as to satisfy equation (1).

$$T \leq V/4F \tag{1}$$

For example, when the thin metal plate 2 is made of stainless steel, the sound speed in the thin metal plate 2 is about 5800 m/s. When the frequency of the vibration generated by the piezo-electric ceramics of the piezo-electric ceramics film 3 is 5 MHz, if 5800 m/s and 5 MHz are substituted for the equation (1), the thickness of the thin metal plate 2 becomes 0.29 mm or smaller. Based on the result, the thickness of the thin metal plate 2 is set to 0.2 mm.

Further, from the viewpoint of improvement of the softness of the heat-resistant ultrasonic sensor 1 to make it flexible, it is possible to confirm the softness of the thin metal plate 2, decide the thickness thereof, substitute the decided thickness and the sound speed in the thin metal plate 2 for equation (1), thereby obtain the frequency F of the vibration generated by the piezo-electric ceramics of the piezo-electric ceramics film 3. And, the thickness of the piezo-electric ceramics film 3 vibrating at the frequency F is decided. The frequency F of the vibration generated by the piezo-electric ceramics of the piezo-electric ceramics film 3 can be decided based on the material of the piezo-electric ceramics and the thickness of the piezo-electric ceramics film 3. Therefore, if the material of the piezo-electric ceramics is decided, the thickness of the piezo-electric ceramics film 3 can be obtained by the frequency F of the vibration.

The piezo-electric ceramics film 3 is formed by the piezo-electric ceramics having a Curie point of 200° C. or higher. The piezo-electric ceramics use lead titanate ($PbTiO_3$), lead zirconate titanate ($Pb(Zr_x, Ti_{1-x})O_3$), lithium niobate ($LiNbO_3$), potassium niobate ($KNbO_3$), bismuth titanate ($Bi_4Ti_3O_{12}$), gallium phosphate ($GaPO_4$), or one kind of substance selected from mixtures of at least two kinds of substances selected from these substances.

The formation of the circular piezo-electric ceramics film 3 on the thin metal plate 2 is performed using one kind of substance (for example, lead titanate) among the aforementioned substances that will be piezo-electric ceramics, by the sol-gel method, as described in Proc. of 2006 IEEE Ultrasonic Symposium "A Piezoelectric Membrane Sensor for Biochemical Monitoring" pp. 800-803, T. IEE Japan, Vol. 121-E, No. 9, (2001) 'Preparation of piezoelectric PZT micro-discs by sol-gel method', and J. Am. Ceram. Soc., 91 [7] pp. 20792082 (2008) 'Low-Temperature Synthesis of Bismuth Titanate by an Aqueous SolGel Method'. The thickness of the piezo-electric ceramics film 3 can be regulated by the coating frequency of gelled liquefied piezo-electric ceramics on the thin metal plate 2, as described in Proc. of 2006 IEEE Ultrasonic Symposium "A Piezoelectric Membrane Sensor for Biochemical Monitoring" pp. 800-803. The piezo-electric ceramics film 3 can be formed directly on the thin metal plate 2. The formation of the piezo-electric ceramics film 3 on the thin metal plate 2 may be performed by a spray coat method (spraying of the liquefied piezo-electric ceramics), a dip method (dipping of the thin metal plate 2 into the liquefied piezo-electric ceramics), or as described in T. IEE Japan, Vol. 121-E, No. 9, (2001) 'Preparation of piezoelectric PZT micro-discs by sol-gel method', the spin coat method.

The thickness of the piezo-electric ceramics film 3 in the present embodiment is, for example, 0.1 mm. The thickness of the piezo-electric ceramics film 3 should be set to 0.5 mm or smaller. If the thickness of the piezo-electric ceramics film 3 exceeds 0.5 mm, when the flexible thin metal plate is bent, the piezo-electric ceramics film 3 is cracked and is separated from the thin metal plate 2 and the function of the heat-resistant ultrasonic sensor 1 disappears. Such a situation can be avoided by reducing the thickness of the piezo-electric ceramics film 3 to 0.5 mm or less. Even in the piezo-electric ceramics film 3 formed by a substance other than lead titanate among the aforementioned substances used to form the piezo-electric ceramics film 3, the thickness should be set to 0.5 mm or less for the aforementioned reason.

The material of the thin metal film 4 is nickel (a nickel alloy included), silver, gold, or platinum and the thickness of the thin metal film 4 is 0.1 mm to 0.2 mm. In the present embodiment, the thickness of the thin metal film 4 is, for example, 0.2 mm. The formation of the thin metal film 4, which is an electrode, on the piezo-electric ceramics film 3 is performed by adhering any metal of nickel (a nickel alloy included), silver, gold, and platinum on the piezo-electric ceramics film 3 by evaporation, plating, sputtering, or screen coating.

The metal wire mesh 5 covers a top surface of the thin metal film 4 and is joined to the thin metal film 4 using any of metal paste, brazing, and high-temperature solder. For the high-temperature solder, solder having a fluxing temperature higher than the highest temperature at the place where the heat-resistant ultrasonic sensor 1 is installed is used. As a material composing the metal wire mesh 5, a material that is resistant to oxidation and corrosion in a high-temperature environment such as nickel (a nickel alloy included), silver, gold, or platinum is used and furthermore, the material is easily connectable to the core 9 of the heat-resistant coaxial cable 7. The respective metal wires composing the metal wire mesh 5 are not a single wire but a stranded wire with a plurality of thin wires stranded. The metal wire mesh 5 is joined to the top surface of the thin metal film 4 using any of metal paste, brazing, and high-temperature solder. A junction material such as metal paste enters between the metal wire mesh 5, so that the metal wire mesh 5 composes an electrode that the flexibility is maintained and electrical continuity can be obtained stably at a high temperature.

The core 9 of the heat-resistant coaxial cable 7 fixed to the thin metal plate 2 with the fixing member 8 is connected to the metal wire mesh 5 at the connection point 6 by any of metal paste, brazing, and high-temperature solder. Furthermore, the fixing member 8 for fixing the heat-resistant coaxial cable 7 to the thin metal plate 2 is fixed to the thin metal plate 2 using any junction material of metal paste, brazing, and high-temperature solder. The ground wire of the heat-resistant coaxial cable 7 is connected to the fixing member 8 that is the ground portion. The electric insulating cover 10 is composed of any of a heat-resistant insulating sheet, a glass fiber, and a ceramics fiber and has a function of electrically insulating the piezo-electric ceramics film 3, the thin metal film 4, the metal wire mesh 5, the connection point 6, the fixing member 8, and the bare cores 9 from the coaxial cable 7, which are the elements of the heat-resistant ultrasonic sensor 1, from the outside member and protecting the piezo-electric ceramics of the piezo-electric ceramics film 3 from destruction. The electric insulating cover 10 may be mechanically fixed to the thin metal plate 2 or may be adhered to the thin metal plate 2 using a heat-resistant adhesive.

The core 9 is knitted in the metal wire mesh 5 and is connected to the metal wire mesh 5. Since the core 9 is knitted in the metal wire mesh 5, the core 9 is not separated from the metal wire mesh 5.

The heat-resistant ultrasonic sensor 1 of the present embodiment forms the piezo-electric ceramics film 3 having a thickness of 0.5 mm or smaller on the flexible thin metal plate 2, so that if the thin metal plate 2 is bent, the thin metal plate 2 and the piezo-electric ceramics film 3 of the heat-resistant ultrasonic sensor 1 can be bent in accordance with the shape of the curved surface of the structural member (for example, a pipe) that is an inspection object and forms a curved surface on the surface and rises in high temperature. Therefore, the greater part (practically the whole surface) of the back opposite to the curved surface of the structural member of the thin metal plate 2 can be made to contact with the curved surface of the structural member and the region of the back of the thin metal plate 2 in contact with the curved surface of the structural member increases remarkably. Concretely, the practically whole surface of the back of the thin metal plate 2 can be made to contact with the curved surface opposite to the back of the structural member via a thin layer of a heat-resistant junction member with a uniform thickness.

In the present embodiment, the thickness of the thin metal film 4 is thin such as 0.1 mm to 0.2 mm, so that no obstacles are caused to bending of the thin metal plate 2 forming the piezo-electric ceramics film 3.

The heat-resistant ultrasonic sensor 1 of the present embodiment using stainless steel for the thin metal plate 2 for forming the piezo-electric ceramics film 3 using lead titanate and having a Curie point of 250° C. can execute an inspection using an ultrasonic wave for a structural body being high temperature up to 200° C. lower than the Curie point. In the aforementioned lead titanate, lithium niobate, potassium niobate, bismuth titanate, and gallium phosphate, the substance having a highest Curie point is lithium niobate and the Curie point thereof is 1200° C., and the substance having a lowest Curie point is lead titanate and the Curie point thereof is 250° C. The heat-resistant ultrasonic sensor 1 having the piezo-electric ceramics film 3 composed of any of those substances, in correspondence to the substance, can execute an inspection using an ultrasonic wave for a structural member in a high temperature state at 200° C. to 1000° C.

The substances capable of being used as piezo-electric ceramics included in the piezo-electric ceramics film 3 are shown in Table 1. In Table 1, the Curie point of the substances capable of being used as piezo-electric ceramics and the working temperature of the substances are shown.

TABLE 1

| Substance name of piezo-electric ceramics | Curie point | Working temperature |
| --- | --- | --- |
| Lead titanate | 250° C. | 200° C. |
| Lead zirconate titanate | 320° C. | 250° C. |
| Lithium niobate | 1200° C. | 1000° C. |
| Potassium niobate | 435° C. | 280° C. |
| Bismuth titanate | 680° C. | 600° C. |
| Gallium phosphate | 970° C. | 800° C. |
| Aluminum nitride | Unknown (Said to be none) | 600° C. or higher |

The core 9 is connected to the metal wire mesh 5 attached to the thin metal film 4 that is an electrode, so that in the present embodiment, the core 9 is not separated from the metal wire mesh 5 and the electrical connection relationship between the core 9 and the thin metal film 4 is not damaged. When the core 9 is directly connected to the thin metal film 4 using an adhesive such as metal paste, the core 9 is apt to be separated from the thin metal film 4, and no voltage can be applied to the piezo-electric ceramics film 3, and no ultrasonic wave can be generated by the piezo-electric ceramics. In the present embodiment where the core 9 is connected to the metal wire mesh 5 attached to the thin metal film 4, a situation that the electrical connection relationship between the core 9 and the thin metal film 4 is not maintained and the generation of an ultrasonic wave in the piezo-electric ceramics stops is not caused.

Further, since the metal wire mesh 5 composed of a stranded wire can stretch and shrink in the axial direction of the metal wire, the thermal expansion difference between the metal wire mesh 5 and the core 9 in a high-temperature state can be absorbed by the metal wire mesh 5. Therefore, the core 9 can be prevented from separation from the metal wire mesh 5 due to the thermal expansion difference. Furthermore, by use of the metal wire mesh 5, even when bending the thin metal plate 2 forming the piezo-electric ceramics film 3 in accordance with the surface having the curved surface of an inspection object to which the heat-resistant ultrasonic sensor 1 is attached, the metal wire mesh 5 is stretched, so that even after the thin metal plate 2 is bent, the electrical connection relationship between the core 9 and the thin metal film 4 can be maintained.

In the present embodiment, although the metal wire mesh 5 is structured using a stranded wire, the metal wire mesh 5 may be structured using a thin wire that is a single wire. Even if the metal wire mesh structured using such a thin wire that is a single wire is used, the similar effect to that of the metal wire mesh 5 structured using a stranded wire can be obtained.

The ultrasonic inspection of the structural member (for example, a pipe) of a power generation plant using the heat-resistant ultrasonic sensor 1 of the present embodiment, for example, a nuclear power plant will be explained by referring to FIG. 3. The thin metal plate 2 of the heat-resistant ultrasonic sensor 1 is bent so as to obtain the same curvature as the curvature of an outer surface of a pipe 12 of a structural member of the nuclear power plant, the structural member being an inspection object to which the heat-resistant ultrasonic sensor 1 is to be attached. Thereafter, an inorganic high-temperature adhesive 11 having a good propagation property of an ultrasonic wave is coated on the back of the thin metal plate 2. The back of the thin metal plate 2 coated with the inorganic high-temperature adhesive 11 is directed toward the outer surface of the pipe 12 to make contact with the outer surface and the heat-resistant ultrasonic sensor 1 is pressed toward the pipe 12. By doing this, the heat-resistant ultrasonic sensor 1 is attached to the outer surface of the pipe 12 that is an inspection object having a curved surface on the surface, by the inorganic high-temperature adhesive 11 that is a heat-resistant junction material. When a measure to prevent the heat-resistant ultrasonic sensor 1 from falling from the pipe 12 is necessary, the heat-resistant ultrasonic sensor 1 may be mechanically fixed to the pipe 12 using a heat-resistant insulating sheet, a glass fiber, or a ceramics fiber. Further, the thin metal plate 2 of the heat-resistant ultrasonic sensor 1 may be attached to the outer surface of the pipe 12 using high-temperature solder in place of the inorganic high-temperature adhesive 11. When joining the thin metal plate 2 to the outer surface of the pipe 12, the thickness of the inorganic high-temperature adhesive 11 or high-temperature solder is made uniform. As a result, the inspection accuracy of the pipe 12 by the heat-resistant ultrasonic sensor 1 is improved.

During the periodic inspection period of an existing nuclear power generation plant, or before starting the first operation in a new nuclear power generation plant, the heat-resistant ultrasonic sensor 1 is attached, as mentioned above, for example, to the pipe 12, which is an inspection object, in the respective nuclear power generation plants. Even after the respective new and existing nuclear power generation plants start operation, the ultrasonic inspection by the heat-resistant ultrasonic sensor 1 is executed continuously for the inspection object such as the pipe 12.

The ultrasonic inspection by the heat-resistant ultrasonic sensor 1 aiming at the pipe 12 will be explained below. The voltage applied by the core 9 of the coaxial cable 7 is applied to the piezo-electric ceramics film 3 through the connection point 6, the metal wire mesh 5, and the thin metal film 4. The piezo-electric ceramics of the piezo-electric ceramics film 3 vibrate due to application of the voltage and generate an ultrasonic wave. The ultrasonic waves are transmitted from the piezo-electric ceramics and enter the pipe 12 through the thin metal plate 2. Due to the incidence of the ultrasonic waves, the reflected waves reflected by the pipe 12 are received by the piezo-electric ceramics of the piezo-electric ceramics film 3. The piezo-electric ceramics output a received signal due to reception of the reflected wave. The received signal passes through the thin metal film 4, the metal wire mesh 5, and the connection point 6 and furthermore, enters the ultrasonic wave transmitter-receiver described later through the core 9 of the heat-resistant coaxial cable 7.

When the nuclear power generation plant is in operation, the pipe 12 is heated to 100° C. to 300° C. by reactor water internally flowing. However, since the heat-resistant ultrasonic sensor 1 uses the thin metal plate 2 and forms piezo-electric ceramics all over the surface of the thin metal plate 2 using lead titanate having a Curie point of 250° C., even when the nuclear power generation plant is in operation in a state that the heat-resistant ultrasonic sensor 1 is attached to the pipe 12, the ultrasonic wave inspection for the pipe 12 rising up to a high temperature of 200° C. can be executed. To execute an ultrasonic wave inspection for the pipe 12 rising up to a higher temperature of 300° C., piezo-electric ceramics having a higher Curie point such as lithium niobate, potassium niobate, bismuth titanate, gallium phosphate, or aluminum nitride must be formed. The heat-resistant ultrasonic sensor 1 is attached to the structural member of the nuclear power generation plant such as the pipe 12, thus even when the nuclear power generation plant is in operation, the soundness of the structural member can be monitored. Further, if wall thinning or cracking is caused to the structural member, when the nuclear power generation plant is in operation, the extent of propagation of wall thinning or cracking can be monitored.

Particularly, since the thin metal plate (flexible metal plate) 2 with a thickness of 0.1 mm is used to form the piezo-electric ceramics film 3 with a thickness of 0.1 mm all over the surface of the thin metal plate 2, the piezo-electric ceramics film 3 is not cracked and the thin metal plate 2 forming the piezo-electric ceramics film 3 can be bent freely. Therefore, as aforementioned, the thin metal plate 2 forming the piezo-electric ceramics film 3 can be bent in accordance with the curvature of the outer surface of the pipe 12, that is, at the same curvature as the curvature of the outer surface of the pipe 12. The thin metal plate 2 bent in accordance with the shape of the curvature of the outer surface of the pipe 12 that is an inspection object is disposed along the curved surface of the outer surface of the pipe 12 and can be attached to the curved surface, so that the ultrasonic wave generated in the piezo-electric ceramics of the piezo-electric ceramics film 3 can efficiently enter the pipe 12 from the curved surface of the outer surface of the pipe 12 and the reflected wave generated by reflection of the incident ultrasonic wave at a defect (wall thinning, cracking, etc.) developed in the pipe 12 can be received efficiently by the piezo-electric ceramics. Further, the thin metal plate 2 and the piezo-electric ceramics film 3 having a Curie point of 200° C. or higher exist, so that the heat-resistant ultrasonic sensor 1 can be attached to the curved surface of the pipe 12 being high temperature when the nuclear power generation plant is in operation, as mentioned above. Therefore, even when the nuclear power generation plant is in operation, the heat-resistant ultrasonic sensor 1 can accurately detect a defect (wall thinning, cracking, etc.) developed in the pipe 12 and can accurately monitor the extent of propagation of the defect. Particularly, the thickness of the inorganic high-temperature adhesive 11 that is disposed between the thin metal plate 2 and the outer surface of the pipe 12 and attaches the thin metal plate 2 to the outer surface of the pipe 12 can be made uniform in front of the back of the thin metal plate 2. Therefore, the detection accuracy of the defect (wall thinning, cracking, etc.) developed in the pipe 12 by the heat-resistant ultrasonic sensor 1 can be improved more.

As aforementioned, the heat-resistant ultrasonic sensor 1 of the present embodiment has a thin and flexible structure using the thin metal plate 2, the thin metal film 4, and the metal wire mesh 5, so that the own weight of the heat-resistant ultrasonic sensor 1 can be reduced. Therefore, the heat-resistant ultrasonic sensor 1 can be handled easily and can be attached easily to a structural member that is an inspection object such as the pipe 12. Further, to attach the heat-resistant ultrasonic sensor 1 to a structural member that is an inspection object such as the pipe 12, large pressing force for plastic-deforming a soft cushioning metal plate as described in Japanese Patent Application Laid-open No. 11(1999)-304777 is not necessary. Further, in the present embodiment, the use of a shoe is not necessary.

In the power generation plant and chemical plant, a thermal insulating material is often attached to the outer surfaces of the pipe and container that rise in high temperature. The heat-resistant ultrasonic sensor 1 of the present embodiment can be attached to the outer surface of the pipe or container that are surrounded by the thermal insulating material, detects a defect (wall thinning, cracking, etc.) of the pipe or container and monitors the propagation of the defect when the plant is in operation.

The attachment of the heat-resistant ultrasonic sensor 1 to the outer surface of the pipe or container that is surrounded by the thermal insulating material material will be explained by referring to FIG. 4 aiming at the pipe.

For example, in the nuclear power generation plant, a thermal insulating material 13 is disposed on the outer surface of the pipe 12 so as to surround this outer surface and is attached to the pipe 12. For such a pipe 12, the heat-resistant ultrasonic sensor 1 is disposed between the pipe 12 and the thermal insulating material 13 and is attached to the curved surface of the outer surface having the curved surface of the pipe 12, as aforementioned. When attaching the heat-resistant ultrasonic sensor 1 to the outer surface of the pipe 12, the thermal insulating material 13 in the attaching place is removed from the pipe 12, and as aforementioned, the thin metal plate 2 of the heat-resistant ultrasonic sensor 1 is bent in accordance with the curvature of the outer surface of the pipe 12, and for example, the bent thin metal plate 2 is attached to the outer surface of the pipe 12 by the inorganic high-temperature adhesive 11. After the attachment of the heat-resistant ultrasonic sensor 1 to the outer surface of the pipe 12 by the inorganic high-temperature adhesive 11 is finished, the heat-resistant ultrasonic sensor 1 is fixed to the pipe 12 using a preliminary fixture 14 such as a heat-resistant insulating sheet, a glass fiber, and a ceramics fiber. Thereafter, the removed thermal insulating material 13 is attached to the pipe 12. At this time, the heat-resistant ultrasonic sensor 1 is covered with the thermal insulating material 13. When attaching the heat-resistant ultrasonic sensor 1 to the pipe 12, the preliminary fixture 14 may not be used.

The heat-resistant coaxial cable 7 that has the core 9 connected to the metal wire mesh 5 of the heat-resistant ultrasonic sensor 1 is taken out outside the thermal insulating material 13 from the joint of the thermal insulating material 13 in the axial direction of the pipe 12 through the interval between the pipe 12 and the thermal insulating material 13, and is connected to an ultrasonic wave transmitter-receiver 15. The ultrasonic wave transmitter-receiver 15 is connected to a data collector 16.

As aforementioned, the thin metal plate 2 forming the piezo-electric ceramics film 3 can be bent in accordance with the curvature of the outer surface of the pipe 12, so that the heat-resistant ultrasonic sensor 1 with a thin thickness can be disposed easily between the pipe 12 and the thermal insulating material 13. Thus, detection of a defect (wall thinning, cracking, etc.) of the pipe 12 covered with the thermal insulating material 13 and becoming a high-temperature state, and monitoring of the defect can be performed using the heat-resistant ultrasonic sensor 1 when the nuclear power generation plant is in operation.

As aforementioned, the ultrasonic wave generated by the piezo-electric ceramics of the piezo-electric ceramics film 3 is entered into the pipe 12. The reflected wave generated in the pipe 12 by the incidence of the ultrasonic wave is received by the piezo-electric ceramics and the received signal of the reflected wave is output. The received signal is input to the ultrasonic wave transmitter-receiver 15 through the core 9 of the heat-resistant coaxial cable 7. The ultrasonic wave transmitter-receiver 15 processes the input received signal and detects whether a defect (wall thinning, cracking, etc.) has been developed in the pipe 12 or not. The ultrasonic wave transmitter-receiver 15 stores information on the input received signal and the portion having a defect developed, in the data collector 16.

The wall thinning developed in the pipe 12 can be detected as indicated below. The ultrasonic wave transmitter-receiver 15 inputs a received signal of the reflected wave (a bottom reflection echo) reflected by the inner surface of the pipe 12 and calculates the thickness of the pipe 12 based on the difference between the reception time of the reflected wave and the incidence time of the ultrasonic wave entering the pipe 12 to generate the reflected wave and the sound speed transmitting in the pipe 12. The wall thinning of the pipe 12 can be monitored by measuring the change with time of the calculated thickness.

Further, the detection of cracking caused inside the pipe 12 is performed by installing the heat-resistant ultrasonic sensor 1 in a position of the pipe 12 highly possible to cause cracking and confirming whether an echo has been generated in a position (a position close to the outer surface of the pipe 12) earlier in time than the bottom reflection echo in the pipe 12. The cracking depth (cracking height) can be obtained by obtaining the time difference between the echo from the inside (bottom) of the pipe 12 and the echo caused at the upper end of the crack and multiplying the time difference by the sound speed in the pipe 12.

The material used in the piezo-electric ceramics film 3 of the heat-resistant ultrasonic sensor 1 may be set in correspondence to the temperature of the structural member of the plant to which the heat-resistant ultrasonic sensor 1 is attached. For example, in a boiling water nuclear power generation plant, on the downstream side of the final stage of the high-pressure feed water heater of the feed water pipe connected to the reactor, the temperature of the feed water pipe becomes 210° C. in operation, so that the piezo-electric ceramics film 3 of the heat-resistant ultrasonic sensor 1 to be attached to the outer surface of this portion of the feed water pipe uses lead zirconate titanate. Further, since in the boiling water nuclear power generation plant, the recirculation pipe and main steam pipe that are connected to the reactor become about 280° C. in operation, the piezo-electric ceramics film 3 of the heat-resistant ultrasonic sensor 1 to be attached to the outer surfaces of these pipes uses bismuth titanate. In a pressurized water nuclear power generation plant, the primary cooling water pipe connected to the reactor and steam generator becomes 320° C. in operation, so that the piezo-electric ceramics film 3 of the heat-resistant ultrasonic sensor 1 attached to the outer surface of the primary cooling water pipe uses bismuth titanate. In a thermal power generation plant, the temperature of the main steam pipe connected to the boiler becomes 600° C. in operation, so that the piezo-electric ceramics film 3 of the heat-resistant ultrasonic sensor 1 attached to the outer surface of the main steam pipe uses lithium niobate. In addition to the above example, if the heat-resistant ultrasonic sensor 1 has the piezo-electric ceramics film 3 composed of a substance having a Curie point higher than the temperature of each pipe, it can be installed in a plurality of pipes having a temperature lower than the Curie point.

Embodiment 2

Figure 5:
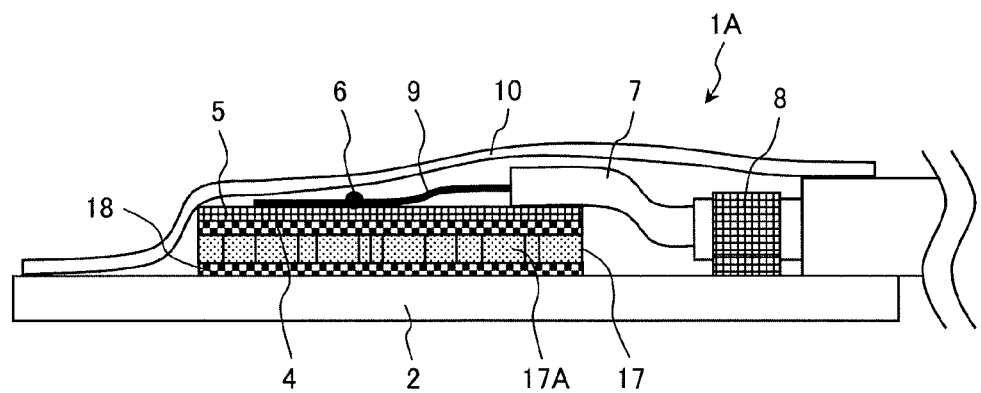
FIG. 5 is a longitudinal sectional view showing a heat-resistant ultrasonic sensor according to embodiment 2, which is another embodiment of the present invention.
Figure 6:
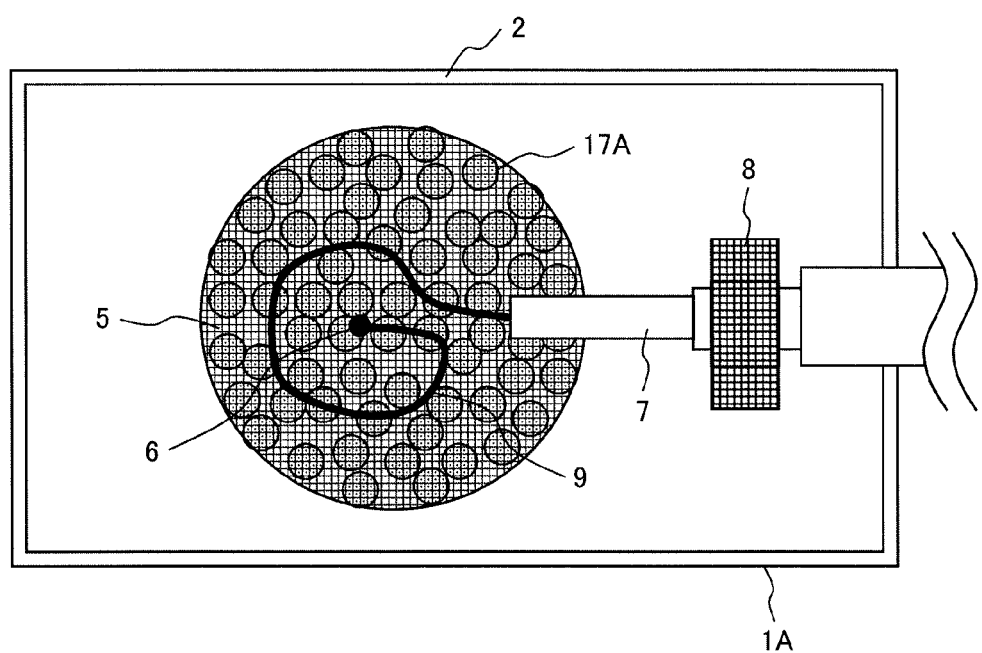
FIG. 6 is a plan view showing a heat-resistant ultrasonic sensor shown in FIG. 5 in a state that an electric insulating cover is removed.

The heat-resistant ultrasonic sensor according to embodiment 2, which is another embodiment of the present invention, will be explained by referring to FIGS. 5 and 6.

A heat-resistant ultrasonic sensor 1A of the present embodiment has a structure that in the heat-resistant ultrasonic sensor 1 of the embodiment 1, the piezo-electric ceramics film 3 has been replaced with a piezo-electric ceramics assembly 17 including a plurality of crystalline piezo-electric ceramics 17A that are small pieces. The other structure of the heat-resistant ultrasonic sensor 1A is the same as that of the heat-resistant ultrasonic sensor 1.

A piece of single-crystal piezo-electric ceramics commercially available is cracked into the small pieces of crystalline piezo-electric ceramics 17A for use. Using an inorganic high-temperature adhesive, an undersurface of each small piece of the crystalline piezo-electric ceramics 17A is adhered to the whole top surface of the thin metal plate 2 and a top surface of it is adhered to an undersurface of the thin metal film 4. A junction portion 18 of the inorganic high-temperature adhesive for joining the undersurface of the crystalline piezo-electric ceramics 17A to the top surface of the thin metal plate 2 is formed on the top surface of the thin metal plate 2. Each small piece of the crystalline piezo-electric ceramics 17A may be adhered to the thin metal plate 2 and the thin metal film 4 by metal paste, brazing, or high-temperature solder in place of the inorganic high-temperature adhesive. The height (equivalent to the thickness of the piezo-electric ceramics film 3 in the embodiment 1) of the piezo-electric ceramics aggregate 17 including the plurality of crystalline piezo-electric ceramics 17A, that is, the height of each small piece of the crystalline piezo-electric ceramics 17A is 0.5 mm that is the same as the thickness of the piezo-electric ceramics film 3 in the embodiment 1. The height of the piezo-electric ceramics assembly 17, that is, the height of each small piece of the crystalline piezo-electric ceramics 17A is 0.5 mm or lower.

The dimension (the diameter of the small piece) of one small piece of crystalline piezo-electric ceramics 17A is decided depending on a radius of curvature of a surface having a curved surface of an inspection object to which the heat-resistant ultrasonic sensor 1A is attached. The representative dimension (the diameter of the small piece) of the small piece of crystalline piezo-electric ceramics 17A is a size of ⅕ or smaller of the radius of curvature of the curved surface of the inspection object, for example, 1.0 mm. Since the diameter of the small piece of crystalline piezo-electric ceramics 17A is set to the size of ⅕ or smaller of the radius of curvature of the curved surface of the inspection object, even when the thin metal plate 2 connected with a number of the small pieces of crystalline piezo-electric ceramics 17A is bent along the curved surface of the inspection object, those small pieces of crystalline piezo-electric ceramics 17A can be prevented from separation from the thin metal plate 2.

The crystalline piezo-electric ceramics 17A are single crystal small piece of any one of lead titanate ($PbTio_3$), lead zirconate titanate ($Pb(Zr_x, Ti_{1-x})O_3$), lithium niobate ($LiNbO_3$), potassium niobate ($KNbO_3$), bismuth titanate ($Bi_4Ti_3O_{12}$), gallium phosphate ($GaPO_4$), and aluminum nitride ($AlN$) that are piezo-electric ceramics having a Curie point of 250° C. or higher.

The interval between each small piece of the crystalline piezo-electric ceramics 17A is in a spatial state with nothing filled. In addition, it is desirable to pour a non-conductive inorganic adhesive into the interval between each small piece of the crystalline piezo-electric ceramics 17A to such an extent as not to disturb the flexibility of the thin metal plate 2 to which each small piece of the crystalline piezo-electric ceramics 17A is attached and fill the mutual interval with the non-conductive inorganic adhesive.

Figure 3:
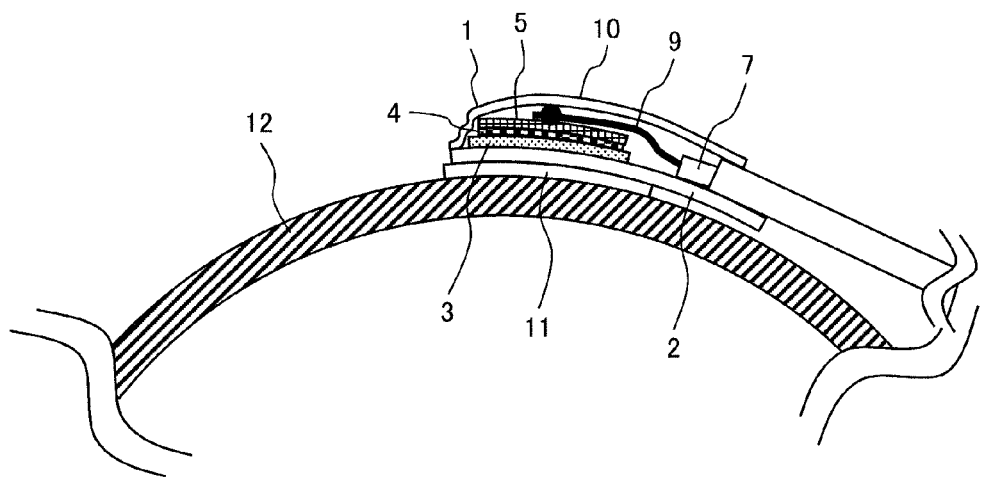
FIG. 3 is an explanatory drawing showing a state that a heat-resistant ultrasonic sensor shown in FIG. 1 is installed on an outer surface having a curved surface of a pipe.
Figure 4:
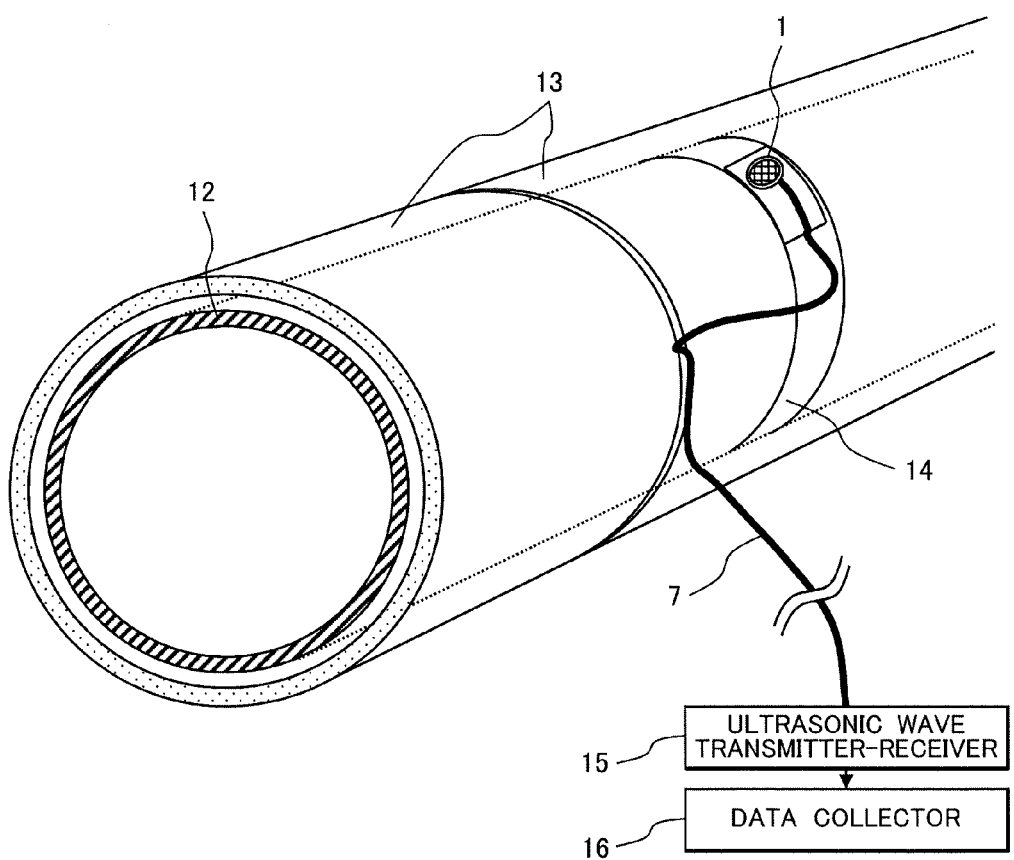
FIG. 4 is an explanatory drawing showing a state that a heat-resistant ultrasonic sensor shown in FIG. 1 is disposed between a pipe on an outer surface whose thermal insulating material is attached and the thermal insulating material.

The heat-resistant ultrasonic sensor 1A of the present embodiment is attached to the surface having the curved surface of the pipe or container of the nuclear power generation plant as shown in FIG. 3 or 4. The heat-resistant ultrasonic sensor 1A detects a defect (wall thinning, cracking, etc.) developed in the pipe or container and monitors the defect.

According to the heat-resistant ultrasonic sensor 1A of the present embodiment, each effect generated in the embodiment 1 can be obtained.

Embodiment 3

Figure 7:
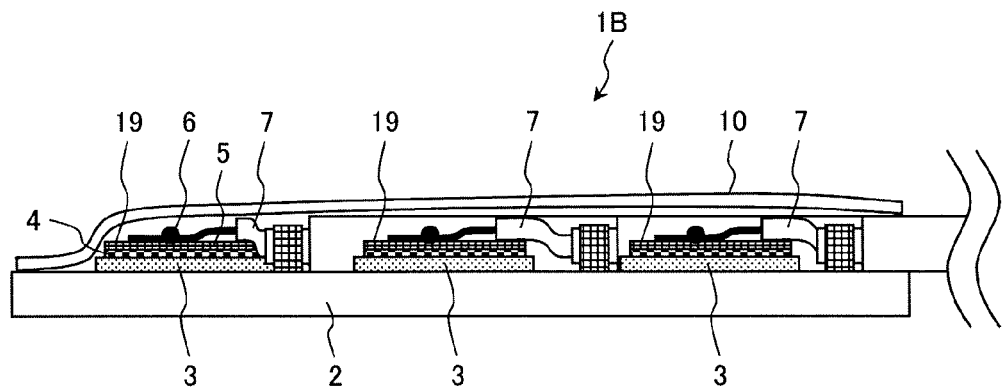
FIG. 7 is a longitudinal sectional view showing a multi channel heat-resistant ultrasonic sensor according to embodiment 3, which is another embodiment of the present invention.
Figure 8:
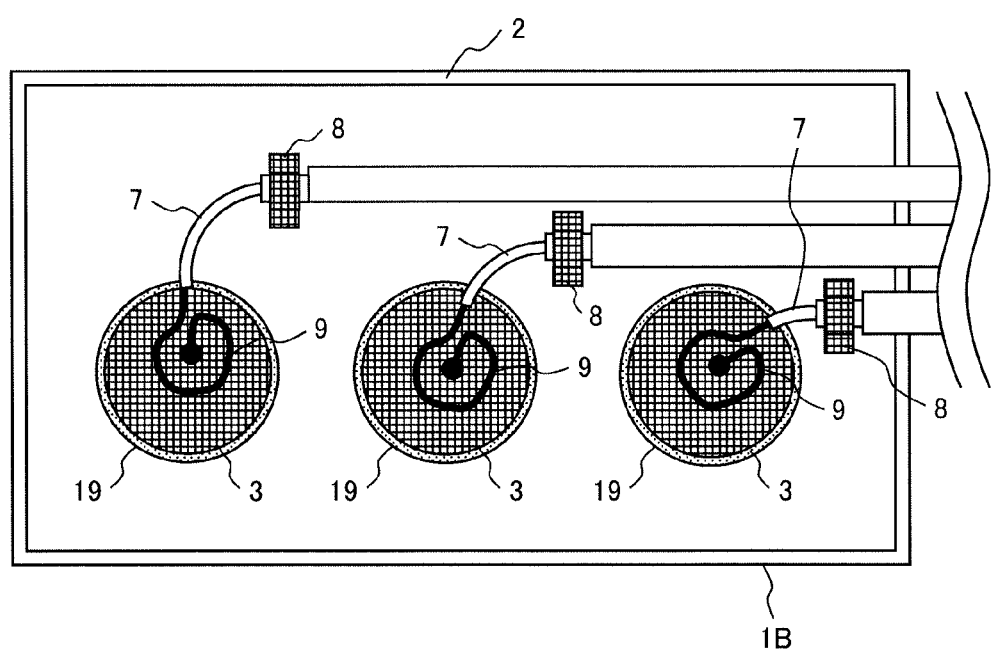
FIG. 8 is a plan view showing a multi channel heat-resistant ultrasonic sensor shown in FIG. 7 in a state that an electric insulating cover is removed.

A multi channel heat-resistant ultrasonic sensor according to embodiment 3, which is still another embodiment of the present invention, will be explained by referring to FIGS. 7 and 8.

The multi channel heat-resistant ultrasonic sensor 1B of the present embodiment practically uses a plurality of heat-resistant ultrasonic sensors 1 of the embodiment 1. In other words, the multi channel heat-resistant ultrasonic sensor 1B has a structure that in the plurality of heat-resistant ultrasonic sensors 1, for example, three heat-resistant ultrasonic sensors 1, the thin metal plate 2 and the electric insulating cover 10 are shared. Concretely, in the multi channel heat-resistant ultrasonic sensor 1B, a plurality of (three for example) heat-resistant piezo-electric element portions 19 are disposed in line on the top surface of the flexible thin metal plate 2 with a thickness of, for example, 0.2 mm and each of the heat-resistant piezo-electric element portions 19 is attached on the top surface of the thin metal plate 2.

Each of the heat-resistant piezo-electric element portions 19 is provided with the piezo-electric ceramics film 3, the thin metal film 4, the metal wire mesh 5, and the coaxial cable 7 as is the case with the heat-resistant ultrasonic sensor 1 of the embodiment 1. The circular piezo-electric ceramics film 3, similarly to the embodiment 1, is formed on the top surface of the thin metal plate 2 by the sol-gel method. In the present embodiment, in relation to the installation of the three heat-resistant piezo-electric element portions 19, three circular piezo-electric ceramics membranes 3 with a thickness of, for example, 0.5 mm are formed on the top surface of the thin metal plate 2 at a predetermined interval. The thin metal film 4 with a thickness of 0.2 mm is installed on the piezo-electric ceramics film 3 and the metal wire mesh 5 is attached on the top surface of the thin metal film 4. The core 9 of the heat-resistant coaxial cable 7 fixed to the thin metal plate 2 by the fixing member 8 is connected to the metal wire mesh 5 at the connection point 6.

The electric insulating cover 10 is attached to the thin metal plate 2 and covers each of the heat-resistant piezo-electric element portions 19.

The multi channel heat-resistant ultrasonic sensor 1B of the present embodiment is attached to the outer surface of the pipe 12 of the nuclear power generation plant as shown in FIG. 3 after the thin metal plate 2 is bent in accordance with the curvature of the outer surface of the pipe 12 of the structural member that is an inspection object. In addition, in the pipe 12 surrounded by the thermal insulating material 13, the multi channel heat-resistant ultrasonic sensor 1B is disposed between the thermal insulating material 13 and the pipe 12 and is attached to the outer surface of the pipe 12 in the state that the thin metal plate 2 is bent at the curvature of the outer surface of the pipe 12, as shown in FIG. 4.

The present embodiment can obtain each effect generated in the embodiment 1. Further, in the present embodiment, since the multi channel heat-resistant ultrasonic sensor 1B has the plurality of (three for example) heat-resistant piezo-electric element portions 19, it is possible to detect and monitor defects (wall thinning, cracking, etc.) at several places when the nuclear power generation plant is in operation for the structural member that is a inspection object such as the pipe 12.

In each of the heat-resistant piezo-electric element portions 19 of the multi channel heat-resistant ultrasonic sensor 1B, the piezo-electric ceramics assembly 17 having the plurality of small piece of crystalline piezo-electric ceramics 17A used in the heat-resistant ultrasonic sensor 1A of the embodiment 2 may be used in place of the piezo-electric ceramics film 3.

Embodiment 4

Figure 9:
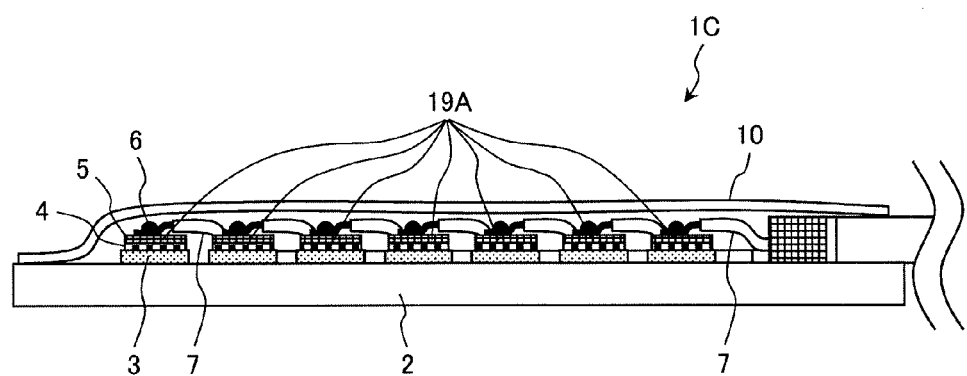
FIG. 9 is a longitudinal sectional view showing a multi channel heat-resistant ultrasonic sensor according to embodiment 4, which is another embodiment of the present invention.
Figure 10:
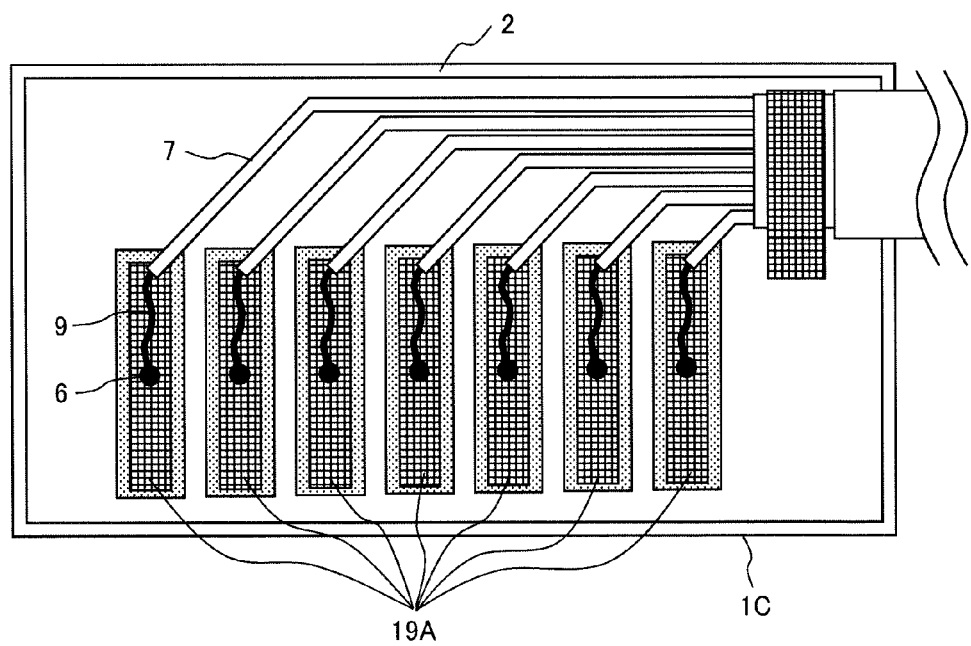
FIG. 10 is a plan view showing a multi channel heat-resistant ultrasonic sensor shown in FIG. 9 in a state that an electric insulating cover is removed.

A multi channel heat-resistant ultrasonic sensor according to embodiment 4, which is another embodiment of the present invention, will be explained by referring to FIGS. 9 and 10.

The multi channel heat-resistant ultrasonic sensor 10 of the present embodiment has a plurality of (seven for example) heat-resistant piezo-electric element portions 19A as the multi channel heat-resistant ultrasonic sensor 1B of the embodiment 3. The heat-resistant piezo-electric element portions 19A are the ones that the circular heat-resistant piezo-electric element portions 19 used in the multi channel heat-resistant ultrasonic sensor 1B are changed to rectangular and the structure of the heat-resistant piezo-electric element portions 19A is the same as that of the heat-resistant piezo-electric element portions 19. Namely, each of the heat-resistant piezo-electric element portions 19A is provided with the piezo-electric ceramics film 3, the thin metal film 4, the metal wire mesh 5, and the coaxial cable 7. The piezo-electric ceramics film 3 of each of the heat-resistant piezo-electric element portions 19A is formed on the top surface of the thin metal plate 2 at intervals by the sol-gel method. These heat-resistant piezo-electric element portions 19A are covered with the electric insulating cover 10 attached to the thin metal plate 2. In the present embodiment, the respective shapes of the piezo-electric ceramics film 3, the thin metal film 4, and the metal wire mesh 5 are rectangular. The seven heat-resistant piezo-electric element portions 19A are disposed on the top surface of the thin metal plate 2 in parallel.

The multi channel heat-resistant ultrasonic sensor 1C of the present embodiment is attached to the outer surface of the pipe 12 of the nuclear power generation plant as shown in FIG. 3 after the thin metal plate 2 is bent in accordance with the curvature of the outer surface of the pipe 12 of the structural member that is an inspection object. Further, in the pipe 12 surrounded by the insulation material 13, the multi channel heat-resistant ultrasonic sensor 10 is disposed between the thermal insulating material 13 and the pipe 12 and is attached to the outer surface of the pipe 12 in the state that the thin metal plate 2 is bent at the curvature of the outer surface of the pipe 12, as shown in FIG. 4.

The present embodiment can obtain each effect generated in the embodiment 1. Further, in the present embodiment, since the multi channel heat-resistant ultrasonic sensor 10 has the plurality of (seven for example) heat-resistant piezo-electric element portions 19A, it is possible to detect and monitor defects (wall thinning, cracking, etc.) at several places when the nuclear power generation plant is in operation for the structural member that is a inspection object such as the pipe 12. Furthermore, by the phased array method or the aperture synthetic method that is a waveform synthetic method, the inside of the inspection object is imaged and the propagation of the defects can be monitored.

In each of the heat-resistant piezo-electric element portions 19 of the multi channel heat-resistant ultrasonic sensor 1B, the piezo-electric ceramics aggregate 17 having the plurality of small piece of crystalline piezo-electric ceramics 17A used in the heat-resistant ultrasonic sensor 1A of the embodiment 2 may be used in place of the piezo-electric ceramics film 3.

The heat-resistant ultrasonic sensors of the embodiment 1 to 4 can be applied to a structural member having a curved surface on the surface that becomes high temperature not only of a nuclear power generation plant such as a boiling water nuclear power generation plant and a pressurized water nuclear power generation plant but also a thermal power generation plant and a chemical plant when they are in operation.

REFERENCE SIGNS LIST 1, 1A, 1B, 1C: heat-resistant ultrasonic sensor, 2: thin metal plate, 3: piezo-electric ceramics film, 4: thin metal film, 5: metal wire mesh, 6: connection point, 7: coaxial cable, 9: core, 10: electric insulating cover, 12: pipe, 13: piezo-electric ceramics film, 15: ultrasonic wave transmitter-receiver, 16: data collector, 17: piezo-electric ceramics assembly, 17A: crystalline piezo-electric ceramics, 19, 19A: heat-resistant piezo-electric element portion.

What is claimed is:

1. A heat-resistant ultrasonic sensor for an ultrasonic inspection comprising
    a flexible metal plate:
    a piezo-electric ceramics portion attached on said flexible metal plate and having a thickness of 0.5 mm or smaller and a Curie point of 200° C. or higher;
    an electrode disposed on said piezo-electric ceramics portion and attached on said piezo-electric ceramics portion;
    a metal wire mesh covering said electrode and attached to said electrode; and
    an electric insulating cover attached to said flexible metal plate and covering said piezo-electric ceramics portion, said electrode, and said metal wire mesh,
    wherein respective metal wires comprising said metal wire mesh are a stranded wire with a plurality of wires stranded.

2. The heat-resistant ultrasonic sensor for an ultrasonic inspection according to claim 1, wherein said piezo-electric ceramics portion is a piezo-electric ceramics film formed on said flexible metal plate.

3. The heat-resistant ultrasonic sensor for an ultrasonic inspection according to claim 1, wherein said piezo-electric ceramics film is a piezo-electric ceramics film formed by the sol-gel method.

4. The heat-resistant ultrasonic sensor for an ultrasonic inspection according to claim 1, wherein said piezo-electric ceramics portion is formed by a plurality of small piece of crystalline piezo-electric ceramics joined to said flexible metal plate.

5. The heat-resistant ultrasonic sensor for an ultrasonic inspection according to claim 1, wherein a core of a cable is connected to said metal wire mesh so as to maintain electric connection between said core and said metal wire mesh.

6. The heat-resistant ultrasonic sensor for an ultrasonic inspection according to claim 5, wherein said core that maintains said electric connection with said metal wire mesh is knitted in said metal wire mesh.

7. The heat-resistant ultrasonic sensor for an ultrasonic inspection according to claim 5, wherein said connection of said core of said cable and said metal wire mesh is a state in which said core of said cable is knitted in said metal wire mesh.

8. The heat-resistant ultrasonic sensor for an ultrasonic inspection according to claim 1, comprising:
a plurality of piezo-electric element portions including said piezo-electric ceramics portion and said electrode member,
wherein said piezo-electric ceramics portion of said respective piezo-electric element portions is attached on said flexible metal plate; and said electric insulating cover covers said plurality of piezo-electric element portions.

9. The heat-resistant ultrasonic sensor according to claim 1, wherein said electrode has a thickness of 0.1 mm to 0.2 mm.

10. An installation method of a heat-resistant ultrasonic sensor for an ultrasonic inspection, comprising steps of:
bending a flexible metal plate of a heat-resistant ultrasonic sensor that is provided with said flexible metal plate, a piezo-electric ceramics portion attached on said flexible metal plate and having a thickness of 0.5 mm or smaller and a Curie point of 200° C. or higher, an electrode disposed on said piezo-electric ceramics portion, and attached on said piezo-electric ceramics portion, a metal wire mesh covering said electrode, attached on said electrode, and comprised of a plurality of respective stranded metal wires, and an electric insulating cover attached to said flexible metal plate and covering said piezo-electric ceramics portion, said electrode, and said metal wire mesh, in accordance with a curved surface of a structural member of a plant; and
disposing said bent flexible metal plate along said curved surface of said structural member and attaching said bent flexible metal plate to said curved surface.

11. The installation method of a heat-resistant ultrasonic sensor for an ultrasonic inspection according to claim 10 comprising steps of:
removing an thermal insulating material existing on a region of said structural member to which said flexible metal plate of said heat-resistant ultrasonic sensor is attached when said structural member is covered with the thermal insulating material; and
covering said heat-resistant ultrasonic sensor by said thermal insulating material and attaching said thermal insulating material to said structural member after said bent flexible metal plate is attached to said curved surface.

12. The installation method of a heat-resistant ultrasonic sensor according to claim 10, wherein an electrode having a thickness of 0.1 mm to 0.2 mm is used as said electrode.

* * * * *